United States Patent
Brusca et al.

(10) Patent No.: US 11,382,293 B2
(45) Date of Patent: *Jul. 12, 2022

(54) PROLIFIC FLOWERING WATERMELON

(71) Applicant: SYNGENTA PARTICIPATIONS AG, Basel (CH)

(72) Inventors: James P. Brusca, Davis, CA (US); Matt Kinkade, Woodland, CA (US); Sarah Danan, Saint-Pol-de-Léon (FR)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/472,389

(22) PCT Filed: Dec. 18, 2017

(86) PCT No.: PCT/EP2017/083399
§ 371 (c)(1),
(2) Date: Jun. 21, 2019

(87) PCT Pub. No.: WO2018/114859
PCT Pub. Date: Jun. 28, 2018

(65) Prior Publication Data
US 2019/0364783 A1    Dec. 5, 2019

Related U.S. Application Data

(60) Provisional application No. 62/437,187, filed on Dec. 21, 2016.

(51) Int. Cl.
*A01H 6/34* (2018.01)
*A01H 5/08* (2018.01)
*C12Q 1/6895* (2018.01)
*A01H 1/04* (2006.01)

(52) U.S. Cl.
CPC ............ *A01H 6/342* (2018.05); *A01H 1/045* (2021.01); *A01H 5/08* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS 8,859,860 B2 * 10/2014 Tolla ................ A01H 6/342
800/308
9,924,652 B1 * 3/2018 Kinkade ............ A01H 6/342

FOREIGN PATENT DOCUMENTS

| JP | 2013-544518 A | 12/2013 |
| RU | 2012110230 A | 9/2013 |
| RU | 2014101369 A | 7/2015 |
| RU | 2560599 C2 | 8/2015 |
| WO | 200070933 A1 | 11/2000 |
| WO | 2003075641 A1 | 9/2003 |
| WO | 2012069539 A1 | 5/2012 |

OTHER PUBLICATIONS

Wehner Todd C.: "Gene List for Watermelon, 2007", Cucurbit Genetic Cooperative Report 30: 96-120, 2007.
Yi Ren et al: "An integrated genetic map based on four mapping populations and quantitative trait loci associated with economically important traits in watermelon (*Citrullus lanatus*)", BMC Plant Biology, Biomed Central, London, GB vol. 14, No. 1; Jan. 20, 2014.
Douglas C Sanders et al: "Yield Response of Watermelon to Planting Density, Planting Pattern, and Polyethylene Mulch", Hortscience, vol. 34, No. 7, Dec. 1999.
Dittmar, Peter et al.: "Maximum Potential vegetative and floral Production and Fruit Characteristics of Watermelon pollenizers", Hortsci, Aermican Society for Horticultural Science, US, vol. 44, No. 1, Feb. 2009.
International Search Report for International Patent Application No. PCT/EP2012/083399 dated Apr. 9, 2018.

* cited by examiner

*Primary Examiner* — Anne Kubelik
(74) *Attorney, Agent, or Firm* — Karen A. Magri

(57) ABSTRACT

The present invention relates to novel watermelon plants displaying an increased number of male flowers. The present invention also relates to seeds and parts of said plants, for example fruits. The present invention further relates to methods of making and using such seeds and plants. The present invention also relates to novel genetic determinants associated with an increased number of male flowers and to molecular markers linked to said novel genetic determinants.

12 Claims, 1 Drawing Sheet
Specification includes a Sequence Listing.

Open male flower number per square meter of watermelon genotypes with and without prolific flowering at peak flowering time.
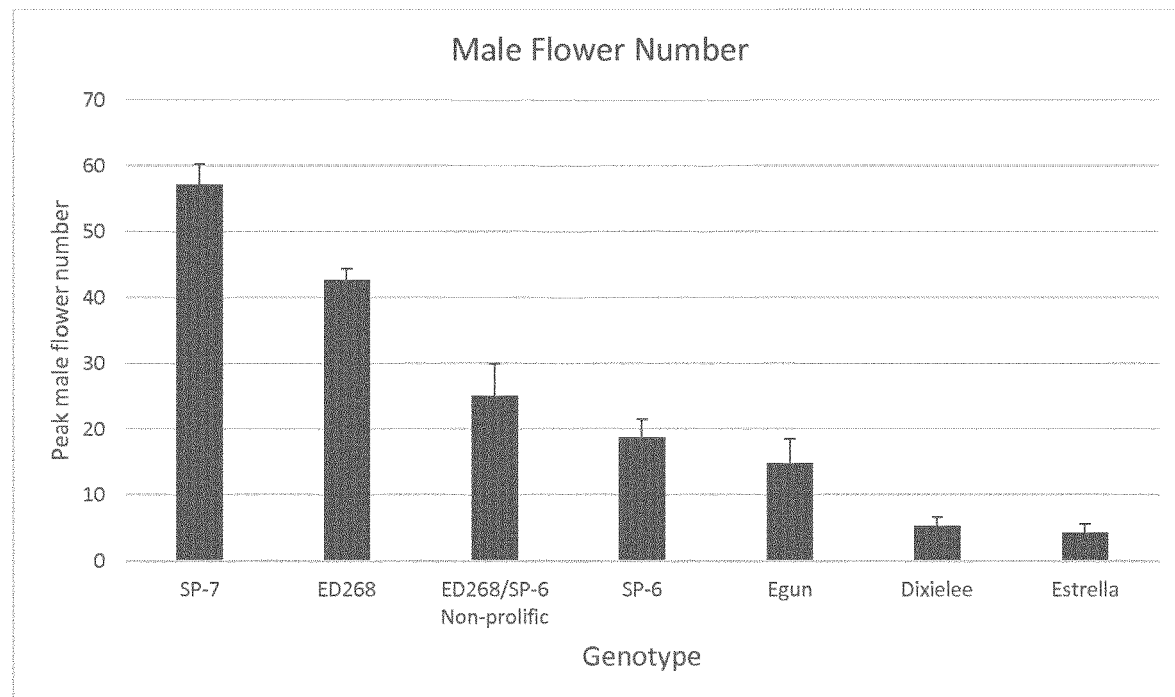

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cgttgagacg ttcgctgttc                                               20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
gacggagacc catgataagg a                                             21

<210> SEQ ID NO 3
<211> LENGTH: 201
<212> TYPE: DNA
<213> ORGANISM: Citrullus lanatus

<400> SEQUENCE: 3
gctcgtagcc gtcgttggtc tctacgccat gtccgctcgc cgccacgtcg agatgccrtc   60
```

```
gttttcgtcg tcgttgagac gttcgctgtt cgtcccttt ggttcctcga ccaccagcgt    120
ctccttatca tgggtctccg tcgtttgcag tcgccgccgg ttctcatcct cacacctgct    180
gccgtcaacc aacgaccctc c                                              201
```

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4

```
ggtcggcaat gactagacga at                                              22
```

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5

```
tcctccatcg ctccaaacct                                                 20
```

<210> SEQ ID NO 6
<211> LENGTH: 201
<212> TYPE: DNA
<213> ORGANISM: Citrullus lanatus

<400> SEQUENCE: 6

```
cgttaaaata aaaaaataaa aaaaataaaa aaagccttta gcagcgacaa atgatagagg    60
gtggtcggca atgactagac gaatggaagc accatgagag aaaaggaggt ttggagcgat    120
ggaggagatc agagatgagg agagggatca aatttgggga ccacgaactc gtggaccccc    180
tccmcgagtt acctgctaag t                                              201
```

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7

```
tcgacaaatg gagaaggttc aact                                            24
```

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8

```
acctttgtgt ccttcccaga a                                               21
```

<210> SEQ ID NO 9
<211> LENGTH: 201
<212> TYPE: DNA
<213> ORGANISM: Citrullus lanatus

<400> SEQUENCE: 9

```
gattgataaa atccacaaca aattcgacaa atggagaagg ttcaacttat ctagaagtgg        60
gagggccact ttatataagt ctattctttc caatcttcca ccatattata tgtctctatt       120
tctaatgcct gaaaaggttg tctctatatt gaaaaagaat aatgcggaac ttcttctggg       180
aaggacacaa aggtagcata a                                                 201
```

PROLIFIC FLOWERING WATERMELON

CROSS-REFERENCE TO RELATED APPLICATIONS

This application is a 371 National Stage application of International Application No. PCT/EP2017/083399, filed Dec. 18, 2017, which claims priority to U.S. 62/437,187 filed Dec. 21, 2016, the entire contents of which applications are hereby incorporated by reference.

FIELD OF THE INVENTION

The present invention relates to novel watermelon plants displaying an increased number of male flowers. The present invention also relates to seeds and parts of said plants, for example fruits. The present invention further relates to methods of making and using such seeds and plants. The present invention also relates to novel genetic determinants associated with an increased number of male flowers and to molecular markers linked to said novel genetic determinants.

BACKGROUND OF THE INVENTION

Watermelon [*Citrullus lanatus* (Thunb.) Matsum and Nakai] is an important specialty crop believed to have originated from Southern Africa in an area near the Kalahari Desert (Dane & Liu, 2007). It is a common crop in all major agriculture production areas and represented a world production of 109,601,914 tonnes in 2013 (derived from data supplied by the Food and Agriculture Organization). The United States is the sixth largest watermelon production country in the world with a production of about 1,771,734 tonnes in 2013, valued up to 483 million of US dollars (USDA Vegetables 2015 Summary).

Majority of the watermelon acreage in the USA are seedless watermelon. Triploid seedless watermelon produces higher yields than the diploid seeded watermelon. The significantly increased watermelon productivity and farm value, as well as decreased production acreage in the USA since the mid-1990s, are the result of using triploid seedless watermelon varieties in commercial production. The planted acreage of seedless watermelon also increases globally as seedless watermelon production usually receives well above the average market price given for seeded watermelons.

Triploid seedless watermelon is a true F1 hybrid between a tetraploid watermelon, as the female parent, and a diploid watermelon, as the male parent (Kihara, 1951). Regular seeded diploid watermelon has 22 chromosomes (2N=2X=22) whereas the tetraploid watermelon has 44 chromosomes (2N=4X=44). When female flowers of the tetraploid watermelon are pollinated by the male flowers of the seeded diploid watermelon plant, the seeds produced in the fruit of the tetraploid plant are triploid hybrid seeds. The triploid hybrid plants grown from the triploid seeds are self-infertile due to the inability of the triploid zygote to produce normal viable gametes (Fehr, 1987). Consequently, to ensure seedless watermelon fruit production, the triploid hybrid plants must be pollinated by the pollen of diploid watermelon plants, called diploid pollenizer plants, which are therefore inter-planted with the triploid hybrid plants in the same field.

To provide adequate pollinization of seedless watermelon plants, it is current practice to inter-plant diploid pollenizer plants over approximately 25-33% of the field surface (e.g. WO 2003/075641, Table 2). The remaining portion of the field is planted with the triploid plants. Thus, to maximize the value of the crop in the field, growers use high yield marketable diploid watermelon varieties, which ultimately compete with the triploid seedless varieties for sun, nutrients, and space. Because pollination of the triploid seedless watermelon plant is critical to the production of seedless fruits, there is a need for improved pollenizer diploid watermelon plant which would efficiently pollinate the triploid seedless plant while maintaining or increasing the yield of said triploid seedless watermelon plant.

WO 2000/70933 discloses a pollenizer for triploid seedless watermelon producing small and non-marketable fruits. However, the use of this pollenizer reduced the total yield of marketable seedless fruits when compared to the use of a classic pollenizer plant. Also, the fruits of the disclosed pollenizer plant which are not harvested become hosts for future diseases and their seeds will germinate and grow into weeds, thus reducing yields further.

WO 2003/075641 provides for an improved diploid pollenizer watermelon plant which produces small, disposable watermelon fruits. The pollenizer plant also has small leaves allowing the pollenizer to be grown in close proximity to the triploid seedless watermelon plants without competing with them. U.S. Pat. No. 6,759,576 describes SP-1, or Super Pollenizer 1, as one example of such an improved diploid pollenizer plant.

In spite of all efforts to provide for improved diploid pollenizer watermelon plants, stable pollination of triploid seedless watermelon plants is still a major limitation in the production of seedless watermelon fruits and there remains a long-lasted and unmet need for further improved diploid pollenizer watermelon plants.

SUMMARY OF THE INVENTION

The present invention addresses the need for more stable pollination of triploid seedless watermelon plants by including and providing novel watermelon plants comprising a prolific flowering trait. In particular embodiments, the invention discloses novel watermelon plants capable of producing more open male flowers per unit area, optionally during a longer period of time, thereby improving the capability of the watermelon plant to pollinate the triploid seedless plant. The presence of more open male flowers per unit area increases the opportunity for pollination to occur. Therefore, by improving the pollination capability of the diploid watermelon plant, more stable and more complete pollination of the triploid female flowers may occur, which will have a positive impact on triploid fruit yield potential. Furthermore, in some embodiments, increasing the amount of male diploid flowers of the watermelon plant will allow the grower to decrease the ratio of diploid to triploid plants in the field, thereby reducing the cost of production and increasing the efficacy of the use of acreage for the production of triploid seedless watermelon.

In addition to having utility for the pollination of the triploid seedless plant, the invention also has utility for increasing the efficiency of hybrid watermelon seed production, by increasing the proportion of male flowers from the pollen donor compared with male flowers from the pollen acceptor. This is expected to result in a larger proportion of hybrid seed set in uncontrolled production.

Altogether, the characteristics of the prolific flowering watermelon plant disclosed within the present invention provide a watermelon grower with novel solutions to enhance economic and commercial efficiency when using a diploid pollenizer watermelon plant for the production of triploid seedless watermelon fruits or the production of hybrid watermelon seed.

The prolific flowering trait is supported by three discrete, heritable genetic determinants causing an increase in the number of open male flowers and which are located on chromosomes 1, 3 and 7 respectively. These genetic determinants have been found to together control/direct the prolific flowering trait. The present invention further discloses specific molecular markers which are linked to these novel genetic determinants and which allow the identification and introgression of the determinants into any desirable plant background.

In a first embodiment, a prolific flowering watermelon plant comprising three genetic determinants directing or controlling the expression of the prolific flowering trait is provided, wherein said prolific flowering plant produces at least 40 open male flowers per square meter at peak flowering time.

In a further embodiment, a watermelon plant according to any of the preceding embodiments comprises three genetic determinants which are genetically or physically linked to 3 marker loci which co-segregate with the prolific flowering trait and are selected in the group comprising marker loci IIH2119, IIH5250 and IIH4836, respectively.

In a further embodiment, the watermelon plant of the invention is a watermelon plant according to any of preceding embodiments, wherein said genetic determinants are genetically or physically linked to marker loci IIH2119, IIH5250 and IIH4836, respectively, and wherein:
a) marker locus IIH2119 can be identified in a PCR by amplification of a DNA fragment with the pair of oligonucleotide primers: forward primer of SEQ ID NO: 1 and reverse primer of SEQ ID NO: 2, and probe of SEQ ID NO: 3,
b) marker locus IIH5250 can be identified in a PCR by amplification of a DNA fragment with the pair of oligonucleotide primers: forward primer of SEQ ID NO: 4 and reverse primer of SEQ ID NO: 5, and probe of SEQ ID NO: 6,
c) marker locus IIH4836 can be identified in a PCR by amplification of a DNA fragment with the pair of oligonucleotide primers: forward primer of SEQ ID NO: 7 and reverse primer of SEQ ID NO: 8, and probe of SEQ ID NO: 9.

In a further embodiment, the watermelon plant of the invention is a watermelon plant according to any of the preceding embodiments, wherein said genetic determinants are obtainable from a donor plant which has the genetic background of watermelon line SP-7, representative seed of which is deposited under ATCC Accession No. PTA-123747, or a progeny or an ancestor thereof.

In a further embodiment, the watermelon plant of the invention is a watermelon plant according to any of the preceding embodiments, wherein watermelon line SP-7, or a progeny or an ancestor thereof, is the source of said prolific flowering genetic determinants, and wherein a representative seed of line SP-7 has been deposited under ATCC Accession No. PTA-123747.

In a further embodiment, the watermelon plant of the invention is a watermelon plant according to any of preceding embodiments, wherein said plant is obtained by crossing watermelon line SP-7, representative seed of which is deposited under ATCC Accession No. PTA-123747, or a progeny or an ancestor thereof, with a watermelon plant that does not contain the prolific flowering genetic determinants.

In a further embodiment, the watermelon plant of the invention is a watermelon plant according to any of preceding embodiments, wherein said plant is an inbred, a dihaploid, a hybrid, a triploid or a tetraploid plant.

It is a further embodiment to provide a plant part, organ or tissue obtainable from a watermelon plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the prolific flowering traits according to the invention, particularly when grown into a plant that produces fruits.

It is a further embodiment to provide a seed of a watermelon plant according to any one of the preceding embodiments.

In another embodiment is considered the use of a watermelon plant, plant part or seed according to any of the preceding embodiments for producing and harvesting triploid seedless fruits.

In another embodiment the invention relates to the use of a watermelon plant, plant part or seed according to any embodiments, wherein the watermelon plant, plant part or seed is watermelon line SP-7, representative seed of which is deposited under ATCC Accession No. PTA-123747, or a progeny or an ancestor thereof.

In another embodiment the invention relates to a method of providing a prolific flowering watermelon plant, plant part or seed, wherein said method comprises the following steps:
a) Crossing a $1^{st}$ plant lacking the prolific flowering genetic determinants with a $2^{nd}$ watermelon plant according to any embodiments,
b) Obtaining a progeny watermelon plant, and,
c) Optionally, selecting a plant of said progeny characterized in that said plant produces at least 40 open male flowers at peak flowering time.

In a further embodiment the invention relates to the method of the preceding embodiment wherein the $2^{nd}$ watermelon plant is watermelon line SP-7, representative seed of which is deposited under ATCC Accession No. PTA-123747, or a progeny or an ancestor thereof.

In another embodiment the invention relates to a method for producing a prolific flowering watermelon plant comprising the following steps:
a) Providing seeds of a watermelon plant according to any of the preceding embodiments,
b) Germinating said seed and growing a mature, fertile plant therefrom,
c) Inducing self-pollination of said plant under a), growing fruits and harvesting the fertile seeds therefrom, and
d) Growing plants from the seeds harvested under c) and selecting a prolific flowering watermelon plant.

In another embodiment the invention relates to a method of identifying a watermelon plant comprising three genetic determinants which are genetically or physically linked to 3 marker loci which co-segregate with the prolific flowering trait and are selected in the group comprising marker loci IIH2119, IIH5250 and IIH4836, respectively, wherein said watermelon plant produces at least 40 open male flowers at peak flowering time, and wherein said method comprises the steps of:
a) providing a population segregating for the prolific flowering trait, b) screening the segregating population for a member comprising a prolific flowering trait, wherein said trait can be identified by the presence of 3 marker loci, which co-segregate with the prolific flowering trait and are marker loci IIH2119, IIH5250 and IIH4836, c) selecting one member of the segregating population, wherein said member comprises the prolific flowering trait.

In another embodiment the invention relates to a method for increasing the number of male flowers of a watermelon plant, comprising the steps of:

a) selecting a watermelon, which comprises a prolific flowering trait, wherein said prolific flowering trait is associated with three genetic determinants capable of directing or controlling expression of said prolific flowering trait in the watermelon plant, wherein said trait can be identified by the presence of 3 marker loci, which co-segregate with the prolific flowering trait and are selected in the group comprising marker loci IIH2119, IIH5250 and IIH4836 or by any adjacent marker locus that is statistically correlated and thus co-segregates with the prolific flowering trait;

b) crossing said plant of step a), which comprises a prolific flowering trait, with a watermelon plant, particularly a cultivated watermelon plant, which does not comprise a prolific flowering trait and shows lower number of male flowers, as compared to the plant of step a), and c) selecting progeny from said cross which shows increased number of male flowers, as compared to the plant of step b), and demonstrates association of the prolific flowering trait with 3 marker loci IIH2119, IIH5250 and IIH4836 of step a).

BRIEF DESCRIPTION OF THE DRAWINGS

FIG. 1 shows the number of open male flowers per square meter at peak flowering time for different genotypes that were grown in Woodland, Calif.

DETAILED DESCRIPTION OF THE INVENTION

Embodiments

In a 1$^{st}$ embodiment, the invention relates to a watermelon plant, particularly a cultivated watermelon plant, more particularly a diploid pollenizer type watermelon plant, wherein said plant comprises three genetic determinants together directing or controlling the expression of the prolific flowering trait, and wherein said prolific flowering plant produces at least 40 open male flowers per square meter at peak flowering time. In a further embodiment, said prolific flowering plant produces at least 45, more preferably at least 50 open male flowers per square meter at peak flowering time.

In another embodiment, the invention relates to a watermelon plant, particularly a cultivated watermelon plant, more particularly a diploid pollenizer type watermelon plant, wherein said plant comprises three genetic determinants directing or controlling the expression of the prolific flowering trait, and wherein said prolific flowering plant produces 30% more open male flowers per square meter at peak flowering time compared with a watermelon plant lacking said three genetic determinants. In a further embodiment, said prolific flowering plant produces 50%, more preferably 70% but even more preferably 100% more open male flowers per square meter at peak flowering time compared with a watermelon plant lacking said genetic determinants.

In another embodiment, the invention relates to a watermelon plant comprising three genetic determinants directing or controlling the expression of the prolific flowering trait, wherein said combined three genetic determinants lead to an increased number of open male flowers per square meter at peak flowering time as compared to an isogenic watermelon plant not comprising said three genetic determinants.

In a further embodiment, the three genetic determinants of the present invention are located on chromosomes 1, 3 and 7, respectively.

In one further embodiment, a watermelon plant according to any of the previous embodiments is provided, wherein the three genetic determinants are genetically or physically linked to 3 marker loci which co-segregate with the prolific flowering trait and are selected in the group comprising marker loci IIH2119, IIH5250 and IIH4836, respectively.

In another embodiment, a watermelon plant, according to any of the preceding embodiments is provided, wherein said genetic determinants are genetically or physically linked to 3 marker loci respectively and wherein:

i. marker locus IIH2119 can be identified in a PCR by amplification of a DNA fragment with the pair of oligonucleotide primers: forward primer of SEQ ID NO: 1 and reverse primer of SEQ ID NO: 2 and probe of SEQ ID NO: 3, ii. marker locus IIH5250 can be identified in a PCR by amplification of a DNA fragment with the pair of oligonucleotide primers: forward primer of SEQ ID NO: 4 and reverse primer of SEQ ID NO: 5 and probe of SEQ ID NO: 6, iii. marker locus IIH4836 can be identified in a PCR by amplification of a DNA fragment with the pair of oligonucleotide primers: forward primer of SEQ ID NO: 7 and reverse primer of SEQ ID NO: 8 and probe of SEQ ID NO: 9.

In another embodiment, the watermelon plant of the invention is a watermelon plant according to any of the preceding embodiments, wherein said plant comprises SEQ ID NO: 3, SEQ ID NO: 6 and SEQ ID NO: 9.

In a further embodiment, the watermelon plant of the invention is a watermelon plant according to any of the preceding embodiments, wherein said genetic determinants are obtainable from a donor plant which has the genetic background of watermelon line SP-7, representative seed of which is deposited under ATCC Accession No. PTA-123747, or a progeny or an ancestor thereof.

In a further embodiment, the watermelon plant of the invention is a watermelon plant according to any of the preceding embodiments, wherein said genetic determinants are as comprised in a donor plant which has the genetic background of watermelon line SP-7, representative seed of which is deposited under ATCC Accession No. PTA-123747, or a progeny or an ancestor thereof.

In a further embodiment, the watermelon plant of the invention is a watermelon plant according to any of the preceding embodiments, wherein watermelon line SP-7, or a progeny or an ancestor thereof, is the source of said prolific flowering genetic determinants, and wherein a representative seed of line SP-7 has been deposited under ATCC Accession No. PTA-123747.

In a further embodiment, the watermelon plant of the invention is a watermelon plant according to any of preceding embodiments, wherein said plant is obtained by crossing watermelon line SP-7, representative seed of which is deposited under ATCC Accession No. PTA-123747, or a progeny or an ancestor thereof, with a watermelon plant that does not contain the prolific flowering genetic determinants.

In a further embodiment, the watermelon plant of the invention is a watermelon plant according to any of the preceding embodiments, wherein said genetic determinants are introgressed from a donor plant which has the genetic background of watermelon line SP-7, representative seed of which is deposited under ATCC Accession No. PTA-123747, or a progeny or an ancestor thereof.

In a further embodiment, the invention relates to a watermelon plant, according to any of the preceding embodiments, comprising three genetic determinants contributing to the prolific flowering trait of the watermelon plant, wherein said genetic determinants are identical to the corresponding alleles present in watermelon line SP-7, representative seed of which is deposited under ATCC Accession No. PTA-123747, or a progeny or an ancestor thereof, which are genetically or physically linked to 3 marker loci in the genome of watermelon line SP-7, representative seed of which is deposited under ATCC Accession No. PTA-123747, or a progeny or an ancestor thereof, which marker loci co-segregate with the prolific flowering trait and can be identified in the genome of watermelon line SP-7, representative seed of which is deposited under ATCC Accession No. PTA-123747, or a progeny or an ancestor thereof, and which marker loci are marker loci IIH2119, IIH5250 and IIH4836.

In an embodiment of the invention, the watermelon plant is a plant according to any of the preceding embodiments, particularly a cultivated watermelon plant, particularly a haploid, a dihaploid, an inbred, a hybrid, a diploid, a triploid or a tetraploid cultivated watermelon plant.

It is a further embodiment to provide a plant part, organ or tissue obtainable from a watermelon plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the prolific flowering traits according to the invention, particularly when grown into a plant that produces fruits.

It is a further embodiment to provide a seed which grows into a watermelon plant according to any one of the preceding embodiments.

In another embodiment the invention relates to the use of a watermelon plant, plant part or seed according to any of the preceding embodiments for producing and harvesting triploid seedless fruits.

In another embodiment the invention relates to the use of a watermelon plant, plant part or seed according to any of preceding embodiments, wherein the watermelon plant, plant part or seed is watermelon line SP-7, representative seed of which is deposited under ATCC Accession No. PTA-123747, or a progeny or an ancestor thereof.

In a further embodiment the invention relates to the use of a watermelon plant according to any of the preceding embodiments to sow a field, a greenhouse, or a plastic house.

In a further embodiment the invention relates to the use of a watermelon plant according to any of the preceding embodiments as a watermelon rootstock. In a further embodiment the invention relates to the use of watermelon line SP-7, representative seed of which is deposited under ATCC Accession No. PTA-123747, or a progeny or an ancestor thereof as a watermelon rootstock.

In a further embodiment the invention relates to the use of the genetic determinants which are genetically or physically linked to 3 marker loci which co-segregate with the prolific flowering trait and are marker loci IIH2119, IIH5250 and IIH4836, respectively to confer the prolific flowering trait to a watermelon plant lacking said trait.

In another embodiment, the plant according to the invention is male sterile.

In another embodiment, the plant according to the invention grows mature watermelon fruits, wherein the interior flesh of said mature fruits are yellow, red, green, orange, or white.

In one embodiment, the invention provides a watermelon plant according to any of the preceding embodiments, which is a hybrid watermelon plant, particularly a cultivated watermelon plant, comprising the prolific flowering genetic determinants.

In one embodiment, the invention provides watermelon fruits produced by a watermelon plant according to any of the preceding embodiments.

In a further embodiment, the genetic determinants are genetically linked to 3 marker loci co-segregating with the prolific flowering trait, wherein said genetic determinants are obtainable from a donor plant having the genetic background of watermelon line SP-7, representative seed of which is deposited under ATCC Accession No. PTA-123747, or a progeny or an ancestor thereof, comprising said genetic determinants and wherein the 3 marker loci, which co-segregate with the prolific flowering trait are marker loci IIH2119, IIH5250 and IIH4836.

The present invention further relates to a watermelon plant seed, particularly a cultivated watermelon plant seed which grows into a watermelon plant according to any of the preceding embodiments.

The invention further relates to the use of a watermelon plant according to any of the preceding embodiments to introgress a prolific flowering trait into a watermelon plant lacking said prolific flowering trait.

The invention further relates to the use of a watermelon plant according to any of the preceding embodiments to sow a field, a greenhouse, or a plastic house.

The invention further relates to the use of a genetic determinant according to any of the herein disclosed embodiments to increase the number of male flowers of a watermelon plant lacking said prolific flowering trait.

The present invention is further directed to a genetic determinant directing or controlling expression of the prolific flowering trait in the watermelon plant. In a further embodiment, the genetic determinants of the present invention are located on chromosome 1, 3 and 7 respectively. In a further embodiment of the present invention, the genetic determinants are obtainable from a donor plant which has the genetic background of watermelon line SP-7, representative seed of which is deposited under ATCC Accession No. PTA-123747, or a progeny or an ancestor thereof, and comprising said genetic determinants.

In a further embodiment, the genetic determinants of the present invention are genetically or physically linked to 3 marker loci, which co-segregate with the prolific flowering trait and are marker loci IIH2119, IIH5250 and IIH4836 or any adjacent marker that is statistically correlated and thus co-segregates with the prolific flowering trait.

In another embodiment, said genetic determinants of the present invention, or functional parts thereof, are genetically linked to 3 marker loci respectively, wherein:
  i. marker locus IIH2119 can be identified in a PCR by amplification of a DNA fragment with the pair of oligonucleotide primers: forward primer of SEQ ID NO: 1 and reverse primer of SEQ ID NO: 2 and probe of SEQ ID NO: 3,
  ii. marker locus IIH5250 can be identified in a PCR by amplification of a DNA fragment with the pair of oligonucleotide primers: forward primer of SEQ ID NO: 4 and reverse primer of SEQ ID NO: 5 and probe of SEQ ID NO: 6,
  iii. marker locus IIH4836 can be identified in a PCR by amplification of a DNA fragment with the pair of oligonucleotide primers: forward primer of SEQ ID NO: 7 and reverse primer of SEQ ID NO: 8 and probe of SEQ ID NO: 9.

The present invention discloses a kit for the detection of the prolific flowering trait locus in a watermelon plant, particularly a cultivated watermelon plant, wherein said kit comprises at least one PCR oligonucleotide primer pair and probe, selected from:
  a. primer pair represented by a forward primer of SEQ ID NO 1 and a reverse primer of SEQ ID NO 2 and probe of SEQ ID NO: 3 or;
  b. primer pair represented by a forward primer of SEQ ID NO 4 and a reverse primer of SEQ ID NO 5 and probe of SEQ ID NO: 6 or;
  c. primer pair represented by a forward primer of SEQ ID NO 7 and a reverse primer of SEQ ID NO 8 and probe of SEQ ID NO: 9 or;
  another primer or primer pair representing an adjacent marker that is statistically correlated and thus co-segregates with the prolific flowering trait.

The present invention also discloses the use of some or all of these DNA markers according to the invention for diagnostic selection and/or genotyping of the prolific flowering trait locus in a watermelon plant, particularly a cultivated watermelon plant, The present invention further discloses the use of some or all of these DNA markers for identifying in a watermelon plant, particularly a cultivated watermelon plant, particularly a watermelon plant according to the invention, the presence of prolific flowering trait locus and/or for monitoring the introgression of the prolific flowering trait locus in a watermelon plant, particularly a cultivated watermelon plant, particularly a watermelon plant according to the invention and as described herein.

The invention further discloses a polynucleotide (amplification product) obtainable in a PCR reaction involving at least one oligonucleotide primer or a pair of PCR oligonucleotide primers selected from the group consisting of SEQ ID NO 1 and SEQ ID NO 2; SEQ ID NO 4 and SEQ ID NO 5; SEQ ID NO 7 and SEQ ID NO 8; and reacting with probes selected from the group comprising SEQ ID NO 3, SEQ ID NO 6 or SEQ ID NO 9 or by another primer representing an adjacent marker that is statistically correlated and thus co-segregates with the prolific flowering trait or with one of the markers disclosed, which amplification product corresponds to an amplification product obtainable from watermelon line SP-7, representative seed of which is deposited under ATCC Accession No. PTA-123747, or a progeny or an ancestor thereof, comprising said genetic determinants, in a PCR reaction with identical primers or primer pairs provided that the respective marker locus is still present in said watermelon plant and/or can be considered an allele thereof.

Also contemplated herein is a polynucleotide that has at least 90%, particularly at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequences of said amplification product obtainable in the above PCR reaction.

The amplification product according to the invention and described herein above can then be used for generating or developing new primers and/or probes that can be used for identifying the prolific flowering trait locus.

The present invention therefore further relates in one embodiment to derived markers, particularly to derived primers or probes, developed from an amplification product according to the invention and as described herein above by methods known in the art, which derived markers are genetically linked to the prolific flowering trait locus.

In another embodiment the invention relates to a method of providing a prolific flowering watermelon plant, plant part or seed, wherein said method comprises the following steps:
  a) Crossing a $1^{st}$ plant lacking the prolific flowering genetic determinants with a $2^{nd}$ watermelon plant according to any embodiments,
  b) Obtaining a progeny watermelon plant, and,
  c) Optionally, selecting a plant of said progeny characterized in that said plant produces at least 40 open male flowers per square meter at peak flowering time.

In another embodiment, the invention relates to the method of preceding embodiment, wherein said plant of step c) produces at least 45, more preferably at least 50 open male flowers per square meter at peak flowering time.

In another embodiment the invention relates to a method of providing a prolific flowering watermelon plant, plant part or seed, wherein said method comprises the following steps:
  a) Crossing a $1^{st}$ plant lacking the prolific flowering genetic determinants with a $2^{nd}$ watermelon plant according to any embodiments,
  b) Obtaining a progeny watermelon plant, and,
  c) Optionally, selecting a plant of said progeny characterized in that said plant produces 30% more open male flowers per square meter at peak flowering time compared with the watermelon plant of step a) lacking said three genetic determinants.

In another embodiment, the invention relates to the method of preceding embodiment, wherein said plant of step c) produces 50%, more preferably 70% but even more preferably 100% more open male flowers per square meter at peak flowering time compared with the watermelon plant of step a) lacking said genetic determinants.

In a further embodiment is considered the method of any of the preceding embodiments wherein the $2^{nd}$ watermelon plant of step a) is watermelon line SP-7, representative seed of which is deposited under ATCC Accession No. PTA-123747, or a progeny or an ancestor thereof.

In another embodiment is considered a method for producing a prolific flowering watermelon plant comprising the following steps:
  a) Providing seeds of a watermelon plant according to any embodiments,
  b) Germinating said seed and growing a mature, fertile plant therefrom,
  c) Inducing self-pollination of said plant under a), growing fruits and harvesting the fertile seeds therefrom, and
  d) Growing plants from the seeds harvested under c) and selecting a prolific flowering watermelon plant.

In a further embodiment, the invention relates to a method for producing a watermelon plant, particularly a cultivated watermelon plant, wherein said watermelon plant has a prolific flowering trait, comprising the steps of:
- a. selecting a watermelon plant, which comprises a prolific flowering trait, wherein said prolific watermelon trait is associated with three genetic determinants capable of directing or controlling expression of said prolific flowering trait in the watermelon plant, wherein said genetic determinants are genetically linked to 3 marker loci, which co-segregate with the prolific flowering trait and are marker loci IIH2119, IIH5250 and IIH4836 or any adjacent marker that is statistically correlated and thus co-segregates with the prolific flowering trait; or with any of the disclosed markers loci,
- b. crossing said plant of step a), which comprises a prolific flowering trait, with a watermelon plant, particularly a cultivated watermelon plant, which does not comprise a prolific flowering trait, and
- c. selecting progeny watermelon plant from said cross which comprises a prolific watermelon trait and demonstrates association with said 3 marker loci of step a) and exhibits prolific flowering.

The present invention further discloses methods of identifying a watermelon plant comprising a prolific flowering trait, comprising the steps of:
- a) providing a population segregating for prolific flowering,
- b) screening the segregating population for a member comprising a prolific flowering trait, wherein said trait can be identified by the presence of 3 marker loci IIH2119, IIH5250 and IIH4836,
- c) selecting one member of the segregating population, wherein said member comprises a prolific flowering trait.

The present invention further discloses methods of identifying a watermelon plant comprising a prolific flowering trait, comprising the steps of:
- a) providing a population segregating for prolific flowering,
- b) screening the segregating population for a member comprising a prolific flowering trait, wherein said trait can be identified by the presence of 3, marker loci, which marker loci are on chromosome 1, 3 and 7 respectively and co-segregate with the prolific flowering trait and can be identified by a PCR oligonucleotide primer or a pair of PCR oligonucleotide primers selected from the group of primer pair represented by a forward primer of SEQ ID NO: 1 and a reverse primer of SEQ ID NO: 2, followed by detection with probe of SEQ ID NO: 3, identifying marker locus IIH2119; primer pair represented by a forward primer of SEQ ID NO: 4 and a reverse primer of SEQ ID NO: 5, followed by detection with probe of SEQ ID NO: 6, identifying marker locus IIH5250; and a primer pair represented by a forward primer of SEQ ID NO: 7 and a reverse primer of SEQ ID NO: 8, followed by detection with probe of SEQ ID NO: 9, identifying marker locus IIH4836,
- c) selecting one member of the segregating population, wherein said member comprises a prolific flowering trait.

In still another embodiment, the invention relates to a prolific flowering-conferring genetic determinant or a prolific flowering-conferring part thereof, which is associated with at least a $1^{st}$ DNA marker represented by a $1^{st}$ pair of PCR oligonucleotide primers comprising forward primer of SEQ ID NO: 1, reverse primer of SEQ ID NO: 2 and probe of SEQ ID NO: 3, and/or at least a $2^{nd}$ DNA marker represented by a $2^{nd}$ pair of PCR primers comprising forward primer of SEQ ID NO: 4, reverse primer of SEQ ID NO: 5 and probe of SEQ ID NO: 6, and/or at least a $3^{rd}$ DNA marker represented by a $3^{rd}$ pair of PCR primers comprising forward primer of SEQ ID NO: 7, reverse primer of SEQ ID NO: 8 and probe of SEQ ID NO: 9, particularly said genetic determinant or a prolific flowering conferring part thereof is spanned by said $1^{st}$, $2^{nd}$ and $3^{rd}$ DNA marker.

In yet another embodiment, the invention relates to the use a DNA marker amplified from the genome of a watermelon plant according to any of the preceding embodiments, preferably from the genome of watermelon line SP-7, representative seed of which is deposited under ATCC Accession No. PTA-123747, or a progeny or an ancestor thereof, by PCR amplification with the pair of oligonucleotide primers: forward primer of SEQ ID NO: 1 and reverse primer of SEQ ID NO: 2 and probe of SEQ ID NO: 3; or forward primer of SEQ ID NO: 4 and reverse primer of SEQ ID NO: 5 and probe of SEQ ID NO: 6; or forward primer of SEQ ID NO: 7 and reverse primer of SEQ ID NO: 8 and probe of SEQ ID NO: 9; wherein said DNA fragment is indicative of the presence of the prolific flowering trait in a watermelon plant, to identify a watermelon plant that comprises and exhibits the prolific flowering trait.

The present invention also relates to the use of prolific flowering-propagating material obtainable from a watermelon plant according to any of the preceding embodiments for growing a watermelon plant in order to produce prolific flowering watermelon plants wherein said prolific flowering may be assessed in a standard assay, particularly an assay as described in Example 2A below.

The present invention also relates to the use of prolific flowering propagating material obtainable from a watermelon plant according to any of the preceding embodiments for producing watermelon fruits.

The present invention also contemplates the use of the prolific flowering genetic determinants of the present invention in association with genetic determinants associated with gynoecia and/or an increased number of female flowers.

It is a further embodiment of the present invention to provide a method for increasing the number of male flowers of a watermelon plant, comprising the steps of:
- a) selecting a watermelon plant, which comprises a prolific flowering trait, wherein said prolific flowering trait is associated with three genetic determinants capable of directing or controlling expression of said prolific flowering trait in the watermelon plant, wherein said trait can be identified by the presence of 3 marker loci, which co-segregate with the prolific flowering trait and are marker loci IIH2119, IIH5250 and IIH4836 or by any adjacent marker that is statistically correlated and thus co-segregates with the prolific flowering trait;
- b) crossing said plant of step a), which comprises a prolific flowering trait, with a watermelon plant, particularly a cultivated watermelon plant, which does not comprise a prolific flowering trait, and
- c) selecting progeny from said cross which shows increased number of male flowers, as compared to the plant of step b), and demonstrates association of the prolific flowering with 3 marker loci IIH2119, IIH5250 and IIH4836 of step a).

It is a further embodiment of the present invention to provide a method for increasing the number of male flowers of a watermelon plant, comprising the steps of:
- a) selecting a watermelon plant, which comprises a prolific flowering trait, wherein said prolific flowering trait is associated with three genetic determinants capable of directing or controlling expression of said prolific flowering trait in the watermelon plant, wherein said trait can be identified by the presence of 3, marker loci, or by any adjacent marker that is statistically correlated and thus co-segregates with the prolific flowering trait;

b) crossing said plant of step a), which comprises a prolific flowering trait, with a watermelon plant, particularly a cultivated watermelon plant, which does not comprise a prolific flowering trait and shows lower number of male flowers, as compared to the plant of step a), and c) selecting progeny from said cross which shows increased number of male flowers, as compared to the plant of step b), and demonstrates association of the prolific flowering with 3 marker loci of step a).

The prolific flowering genetic determinants can also be introduced by way of mutagenesis, for example by way a chemical mutagenesis, for example by way of EMS mutagenesis. Alternatively, the prolific flowering genetic determinants can also be identified and/or introduced by way of using TILLING techniques.

In a further embodiment, the invention relates to the use of the genetic determinants of the invention to manipulate the prolific flowering phenotype in a watermelon plant wherein said manipulation is effected by genetic modification and wherein said genetic modification is introduced by TILLING. Preferably, the genetic determinants of the invention are characterized by the sequences herein disclosed, more preferable by SEQ ID NOs: 3, 6 and 9, representing the target sequences.

The prolific flowering genetic determinants can also be introduced by targeted mutagenesis, e.g. by way of homologous recombination, zinc-finger nucleases, oligonucleotide-based mutation induction, transcription activator-like effector nucleases (TALENs), clustered regularly interspaced short palindromic repeat (CRISPR) systems or any alternative technique to edit the genome.

Alternatively, the prolific flowering genetic determinants can also be introduced by transgenic or cis-genic methods via a nucleotide construct which may be comprised in a vector.

Based on the description of the present invention, the skilled person who is in possession of watermelon line SP-7, representative seed of which is deposited under ATCC Accession No. PTA-123747, or a progeny or an ancestor thereof, comprising said genetic determinants, as described herein, has no difficulty to transfer the said genetic determinants of the present invention to other watermelon plants of various types using breeding techniques well-known in the art with the support of marker loci herein disclosed.

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A "cultivated watermelon" plant is understood within the scope of the invention to refer to a plant that is no longer in the natural state but has been developed and domesticated by human care and for agricultural use and/or human consumption, and excludes wild watermelon accessions, such as *Citrullus lanatus* cv "Egun". As a matter of example, in embodiments, a watermelon plant according to the present invention is capable of growing yellow fruits. Alternatively or additionally, a cultivated watermelon plant according to the invention comprises a brittle rind (e.g., gene e in the homozygous state, as can be found in watermelon line SP-1 (WO 2003/075641)). In further embodiments, the cultivated watermelon plant is a diploid plant, a tetraploid plant and/or a triploid plant.

A "genetic determinant directing or controlling expression" is understood herein to refer to a heritable genetic element that is capable of contributing to the prolific flowering of the plant by influencing expression of this prolific flowering trait on the level of the DNA itself, on the level of translation, transcription and/or activation of a final polypeptide product.

In one preferred embodiment, the genetic determinants contributing to the traits of the plants according to the present invention are native to the *Citrullus* genus. The genetic determinants according to the present invention do not comprise genetically modified events comprising heterologous genetic material and/or genetic material foreign to *Citrullus* genus.

An "allele" is understood within the scope of the invention to refer to alternative or variant forms of various genetic units identical or associated with different forms of a gene or of any kind of identifiable genetic determinant, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

An allele associated with a qualitative trait may comprise alternative or variant forms of various genetic units including those that are identical or associated with a single gene or multiple genes or their products or even a gene disrupting or controlled by a genetic determinant contributing to the phenotype represented by the locus.

A "prolific flowering watermelon" is herein defined as a watermelon plant having a prolific flowering trait which accounts for an increased male flower number compared to a plant lacking said trait.

Relatively speaking, the term "increased male flower number" is herein understood to mean that a plant according to the present invention, i.e. comprising the prolific flowering genetic determinants, is capable of producing at least 40 male flowers per square meter at peak flowering time.

"Peak flowering time" is herein understood as the week when the most open male flowers were recorded across all plots.

The term "trait" refers to a characteristic or a phenotype. In the context of the present invention, a prolific flowering trait is an increased male flower number. A trait may be inherited in a dominant or recessive manner, or in a partial or incomplete-dominant manner. A trait may be monogenic or polygenic, or may result from the interaction of one or more genes with the environment. A watermelon plant can be heterozygous or heterozygous for the trait.

The terms "hybrid", "hybrid plant", and "hybrid progeny" refer to an individual produced from genetically different parents (e.g. a genetically heterozygous or mostly heterozygous individual).

The term "inbred line" refers to a genetically homozygous or nearly homozygous population. An inbred line, for example, can be derived through several cycles of brother/sister breeding or of selfing or in dihaploid production.

The term "dihaploid line" refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially no longer segregating (stable).

The term "cultivar" or "variety" refers to a horticultural derived variety, as distinguished from a naturally occurring variety. In some embodiments of the present invention the cultivars or varieties are commercially valuable.

The term "genetically fixed" refers to a genetic element which has been stably incorporated into the genome of a plant that normally does not contain the genetic element. When genetically fixed, the genetic element can be transmitted in an easy and predictable manner to other plants by sexual crosses.

The term "plant" or "plant part' refers hereinafter to a plant part, organ or tissue obtainable from a watermelon plant according to the invention, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the prolific flowering traits according to the invention, particularly when grown into a plant that produces fruits.

A "plant" is any plant at any stage of development.

A watermelon plant seed is a seed which grows into a watermelon plant according to any of the embodiments.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "watermelon" means any variety, cultivar, or population of Citrullus lanutus.

The marketable fruit "yield", as used herein, refers to the number of harvestable fruits (frt) produced per area of production (frt/Ha).

As used herein, the term "marker allele" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes.

"Heterozygous" is understood within the scope of the invention to refer to unlike alleles at one or more corresponding loci on homologous chromosomes.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene or any other genetic element or factor contributing to a trait.

As used herein, "marker locus" refers to a region on a chromosome, which comprises a nucleotide or a polynucleotide sequence that is present in an individual's genome and that is associated with one or more loci of interest, which may comprise a gene or any other genetic determinant or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "cosegregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome.

"Co-segregation" also refers to the presence of two or more traits within a single plant of which at least one is known to be genetic and which cannot be readily explained by chance.

As used herein, the term "genetic architecture at the quantitative trait locus" refers to a genomic region which is statistically correlated to the phenotypic trait of interest and represents the underlying genetic basis of the phenotypic trait of interest.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

A "genetic marker" can be physically located in a position on a chromosome that is within or outside the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative trait as defined herein). Thus, in some embodiments a genotype comprises a summary of one or more alleles present within an individual at one or more genetic loci of a quantitative trait. In some embodiments, a genotype is expressed in terms of a haplotype (defined herein below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the phrase "quantitative trait" refers to a phenotypic trait that can be described numerically (i.e., quantitated or quantified). A quantitative trait typically exhibits continuous variation between individuals of a population; that is, differences in the numerical value of the phenotypic trait are slight and grade into each other. Frequently, the frequency distribution in a population of a quantitative phenotypic trait exhibits a bell-shaped curve (La, exhibits a normal distribution between two extremes).

A "quantitative trait" is typically the result of a genetic locus interacting with the environment or of multiple genetic loci interacting with each other and/or with the environment. Examples of quantitative traits include plant height and yield.

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the terms "quantitative trait locus" (QTL) and "marker trait association" refer to an association between a genetic marker and a chromosomal region and/or gene that affects the phenotype of a trait of interest. Typically, this is determined statistically; e.g., based on one or more methods published in the literature. A QTL can be a chromosomal region and/or a genetic locus with at least two alleles that differentially affect a phenotypic trait (either a quantitative trait or a qualitative trait).

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower colour, and several known disease resistances such as, for example, Fungus spot resistance or Tomato Mosaic Virus resistance.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

A single nucleotide polymorphism (SNP), a variation at a single site in DNA, is the most frequent type of variation in the genome. A single-nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are the array that contains nucleic acid sequences (ie amplified sequence or target), one or more labeled allele-specific oligonucleotide probes and a detection system that records and interprets the hybridization signal.

The presence or absence of the desired allele may be determined by real-time PCR using double-stranded DNA dyes or the fluorescent reporter probe method.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus *Capsicum* used to characterize genetically a trait in a plant to be tested. Typically, the plant to be tested is crossed with a "tester" plant and the segregation ratio of the trait in the progeny of the cross is scored.

"Probe" as used herein refers to a group of atoms or molecules which is capable of recognising and binding to a specific target molecule or cellular structure and thus allowing detection of the target molecule or structure. Particularly, "probe" refers to a labelled DNA or RNA sequence which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions are for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The "thermal melting point" is the temperature (under defined ionic strength and pH) at which 50% of the target sequence hybridizes to a perfectly matched probe. Very stringent conditions are selected to be equal to the melting temperature (T.sub.m) for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

Seed Deposit Details

Applicant has made a deposit of 2500 seeds of watermelon (diploid *Citrullus lanatus*) line SP-7 under the Budapest Treaty with ATCC, Manassas, Va., USA, on 14 Dec. 2016 under ATCC Accession No. PTA-123747. Applicant elects the expert solution.

BIBLIOGRAPHY

Dane F. and Liu J., 2007, Diversity and origin of cultivated and citron type watermelon (*Citrullus lanatus*), Genetic Resources and Crop Evolution, Volume 54, Issue 6, pp 1255-1265.

Food and Agriculture Organization of the United Nations, Statistics Division, FAOSTAT, http://faostat3.fao.org/browse/Q/*/E.

United States Department of Agriculture, National Agricultural Statistics Service, Vegetables 2015 Summary, http://usda.nnannlib.cornell.edu/usda/current/VegeSunnm/VegeSumm-02-04-2016.pdf.

Kihara H., 1951, Triploid watermelons, Proc. Amer. Soc. Hort. Sci., 58:217-230.

Fehr W. R., 1987, Principles of cultivar development, theory and technique, Vol. 1, Macmillian Publishing Company.

FIGURES

FIG. 1 shows the number of open male flowers at peak flowering time for different genotypes that were grown in Woodland, Calif.

SEQUENCES

SEQ ID NO: 1
5' CGTTGAGACGTTCGCTGTTC 3'

SEQ ID NO: 2
5' GACGGAGACCCATGATAAGGA 3'

SEQ ID NO: 3
5'
GCTCGTAGCCGTCGTTGGTCTCTACGCCATGTCCGCTCGCCGCCACGTCG
AGATGCCRTCGTTTTCGTCGTCGTTGAGACGTTCGCTGTTCGTCCCTTTT
GGTTCCTCGACCACCAGCGTCTCCTTATCATGGGTCTCCGTCGTTTGCAG
TCGCCGCCGGTTCTCATCCTCACACCTGCTGCCGTCAACCAACGACCCTC
C 3'

SEQ ID NO: 4
5' GGTCGGCAATGACTAGACGAAT 3'

SEQ ID NO: 5
5' TCCTCCATCGCTCCAAACCT 3'

SEQ ID NO: 6
5'
CGTTAAAATAAAAAAATAAAAAAAATAAAAAAAGCCTTTAGCAGCGACAA
ATGATAGAGGGTGGTCGGCAATGACTAGACGAATGGAAGCACCATGAGAG
AAAAGGAGGTTTGGAGCGATGGAGGAGATCAGAGATGAGGAGAGGGATCA
AATTTGGGGACCACGAACTCGTGGACCCCCTCCMCGAGTTACCTGCTAAG
T 3'

SEQ ID NO: 7
5' TCGACAAATGGAGAAGGTTCAACT 3'

SEQ ID NO: 8
5' ACCTTTGTGTCCTTCCCAGAA 3'

SEQ ID NO: 9
5'
GATTGATAAAATCCACAACAAATTCGACAAATGGAGAAGGTTCAACTTAT
CTAGAAGTGGGAGGGCCACTTTATATAAGTCTATTCTTTCCAATCTTCCA
CCATATTATATGTCTCTATTTCTAATGCCTGAAAAGGTTGTCTCTATATT
GAAAAAGAATAATGCGGAACTTCTTCTGGGAAGGACACAAAGGTAGCATA
A 3'

EXAMPLES

Example 1: Germplasm and Population Development

A recombinant inbred line (RIL) genetic population was constructed by hybridizing a wild watermelon accession, PI595203, [*Citrullus lanatus* cv "Egun"] with a modern cultivar, PI635731, [*Citrullus lanatus* cv "Dixielee"], self-hybridized using single seed descent until all observable phenotypic traits were fixed and each line exhibited uniform characteristics. The population (also referred to as the ED-RIL population) was cultivated in open field trials and phenotyped for various traits. This resulted in the observation of an extreme phenotype (termed "prolific flowering") which displayed a large increase in male flower number. Line designated as ED268 was the most preferred line for increased number of male flowers. Some ED-RILs expressed prolific flowering while some did not, indicating discrete genetic control of the phenotype. Continued observation of the population revealed that prolific flowering was a heritable trait. Prolific flowering was not observed in either parent, indicating that a specific combination of alleles from both Egun and Dixielee controls the expression of the phenotype. Further research revealed that at least three genetic determinants, one from Egun and two from Dixielee, are involved in the control of prolific flowering.

Line ED268 was selected and crossed with line SP-6 for developing new watermelon plants comprising the prolific flowering trait. The resulting F1 plants were self-hybridized and subsequently fixed, and the resulting lines were again phenotyped for prolific flowering. Some lines expressed the prolific flowering trait (e.g. line SP-7) while some did not (e.g. non-prolific sister line of SP-7), confirming the discrete genetic control of the phenotype. This also confirmed that the prolific flowering trait can be introgressed into different genetic backgrounds.

Line designated as SP-7 was identified as the most preferred line selected for increased number of male flowers and has been retained and deposited at ATCC under Number ATCC PTA-123747 on 14 Dec. 2016. Line SP-7 is fixed for the prolific flowering trait, i.e. line SP-7 comprises the three favorable genetic determinants at the homozygous state.

Example 2: Phenotyping

Example 2A. Method of Measuring Prolific Flowering: Male Flower Number

Plots of each genotype were cultivated in open field conditions with 24 inches (61 cm) spacing between plants. All data are from a field trial set up in a randomized complete block design having three repetitions treated as blocks. Male flower number was estimated by counting the number of open male flowers within a square meter of area. For each plot, two measurements were taken on a weekly basis. Peak flowering time was determined as the week when the most open male flowers were recorded across all plots.

Example 2B. Phenotyping Results

FIG. 1 shows the prolific flowering phenotyping results of the following genotypes: (i) deposited line SP-7 and its ancestors: line SP-6 and line ED268; (ii) line ED268 ancestors: Egun and Dixielee; (iii) a non-prolific sister line of SP-7; and (iv) an unrelated non-prolific line: Estrella.

At peak flowering time, the parents of ED268, Dixielee and Egun, presented only 12.44% and 34.74%, respectively, of the open male flower number that ED268 presented. The non-prolific parent of SP-7, SP-6, presented approximately 32.57% of the number of male flowers that SP-7 presented at peak flowering time. It is also shown that SP-7 has a far greater male flower number than its non-prolific sister line, ED268/SP-6 Non-prolific, which presented only 43.96% of the male flower number that SP-7 presented at peak flowering time. This demonstrates that the prolific flowering trait is a discrete genetic trait which can be selected for or against during the breeding process.

Table 1 further demonstrates how SP-7 differentiates from other non-prolific varieties. Statistical analysis shows that SP-7 is significantly different for the number of male flowers per unit area presented at peak flowering as compared to all other varieties included in these experiments. Further, using Fisher's LSD method, the watermelon genotypes with the prolific flowering trait included in these experiments (SP-7 and ED268) have significantly higher numbers of male flowers per unit area than the watermelon genotypes which do not possess the prolific flowering trait.

TABLE 1 statistical comparison of mean peak flower number per unit area of (i) deposited line SP-7 and its ancestors: line SP-6 and line ED268, (ii) line ED268 ancestors: Egun and Dixielee, (iii) a non-prolific sister line of SP-7 and (iv) an unrelated non-prolific line: Estrella.

| Entry | Mean Peak Male Flower # per square meter | Group |
|---|---|---|
| SP-7 | 57.17 | A |
| ED268 | 42.67 | B |
| ED268/SP-6 (Non-prolific) | 25.17 | C |
| SP-6 | 18.67 | D |
| Egun | 14.83 | D |
| Dixielee | 5.33 | E |
| Estrella | 4.33 | E |

For statistical purposes the mean peak male flower # per square meter was used. A one-way ANOVA showed significant differences between entries (F = 128.083, Df = 6, P < 0.05). A multiple comparison of the means per entry (Fisher's LSD-method) showed significant differences between the different entries (shown as different letters).

Example 3: Genotyping and QTL Discovery

Example 3A. Method of Identifying the Genetic Determinants Underlying the Prolific Flowering Trait For QTL discovery, 166 recombinant inbred lines (RILs) from the "ED-RIL" population were genotyped with 260 genetic markers spanning the genome and a genetic map was calculated. These lines were grown in the open field in Woodland, Calif., using standard growing methods and phenotyped for prolific flowering.

The QTL detection was performed using the R/qtl package in the R statistical framework. First, the function 'calc.genoprob' was used to calculate the genotype probabilities (step 1cM). Haley-Knott regression was performed to provide an approximation of the results of standard interval mapping. Then, the function 'stepwiseqtl' was invoked, which provides a fully automated model selection forward/backward algorithm. LOD threshold for main effect was determine by 10,000 permutations. This algorithm takes into account different possible interactions (e.g., epistasis). The function 'refineqtl' was used to refine the locations of QTL in the context of a multiple QTL model (maximum likelihood estimates). The function 'fitqtl' was used to fit a defined QTL model and obtain estimates of QTL effects. Three QTLs were identified based on the prolific flowering phenotypes (Table 2).

Example 3B. Effect of the QTL Situated on Chromosomes 1, 3, and 7 on Prolific Flowering Table 2 shows the chromosome location, effect of the QTLs, LOD scores, percent of variation explained by each QTL on chromosome 1, 3 and 7 for prolific flowering and the favourable genotype.

TABLE 2

Significant QTLs associated with prolific flowering from the "ED-RIL" population.

| Chromosome location | df | LOD | % var | Pvalue (Chi2) | Favorable genotype |
|---|---|---|---|---|---|
| 1 | 1 | 4.327 | 11.88 | 8.04E−06 | G/G |
| 3 | 1 | 4.131 | 11.30 | 1.29E−05 | A/A |
| 7 | 1 | 4.625 | 12.78 | 3.93E−06 | C/C | df = degrees of freedom,
"LOD" = log likelihood score,
"% var" = percent phenotypic variation explained by the QTL,
"Pvalue(Chi2)" = the probability of each QTL detected due to random chance by chi-square analysis.

Example 3C. QTL Sequence Information

Table 3 shows the nucleotide sequences associated with marker loci IIH2119, IIH5250 and IIH4836, respectively. For each marker loci, the table shows the chromosome location, the primers (forward and reverse) allowing to amplify the marker DNA fragment and the target sequence. For each target sequence, the favourable SNP allele is shown in bold.

TABLE 3

Nucleotide sequences of SEQ ID NO. 1-9.

| Chromosome | Marker loci | Sequence type | Nucleotide sequence | Sequence ID |
|---|---|---|---|---|
| 1 | IIH2119 | Forward primer | CGTTGAGACGTTCGCTGTTC | SEQ ID NO: 1 |
| 1 | IIH2119 | Reverse primer | GACGGAGACCCATGATAAGGA | SEQ ID NO: 2 |
| 1 | IIH2119 | Target sequence | GCTCGTAGCCGTCGTTGGTCTC TACGCCATGTCCGCTCGCCGCC ACGTCGAGATGCCRTCGTTTTC GTCGTCGTTGAGACGTTCGCTG TTCGTCCCTTTT[A/G]GTTCCTC GACCACCAGCGTCTCCTTATCA TGGGTCTCCGTCGTTTGCAGTC GCCGCCGGTTCTCATCCTCACA CCTGCTGCCGTCAACCAACGAC CCTCC | SEQ ID NO: 3 (favourable allele) |

TABLE 3-continued

Nucleotide sequences of SEQ ID NO. 1-9.

| Chromosome | Marker loci | Sequence type | Nucleotide sequence | Sequence ID |
|---|---|---|---|---|
| 3 | IIH5250 | Forward primer | GGTCGGCAATGACTAGACGAAT | SEQ ID NO: 4 |
| 3 | IIH5250 | Reverse primer | TCCTCCATCGCTCCAAACCT | SEQ ID NO: 5 |
| 3 | IIH5250 | Target sequence | CGTTAAAATAAAAAAATAAAAAA AATAAAAAAAGCCTTTAGCAGC GACAAATGATAGAGGGTGGTCG GCAATGACTAGACGAATGGAAG CACCATGAGAG[A/C]AAAGGAG GTTTGGAGCGATGGAGGAGATC AGAGATGAGGAGAGGGATCAAA TTTGGGGACCACGAACTCGTGG ACCCCCTCCMCGAGTTACCTGC TAAGT | SEQ ID NO: 6 (favourable allele) |
| 7 | IIH4836 | Forward primer | TCGACAAATGGAGAAGGTTCAA CT | SEQ ID NO: 7 |
| 7 | IIH4836 | Reverse primer | ACCTTTGTGTCCTTCCCAGAA | SEQ ID NO: 8 |
| 7 | IIH4836 | Target sequence | GATTGATAAAATCCACAACAAAT TCGACAAATGGAGAAGGTTCAA CTTATCTAGAAGTGGGAGGGCC ACTTTATATAAGTCTATTCTTTC CAATCTTCCA[A/C]CATATTATAT GTCTCTATTTCTAATGCCTGAAA AGGTTGTCTCTATATTGAAAAAG AATAATGCGGAACTTCTTCTGG GAAGGACACAAAGGTAGCATAA | SEQ ID NO: 9 (favourable allele) |

What is claimed is:

1. A prolific flowering watermelon plant comprising three genetic determinants directing or controlling the expression of the prolific flowering trait, wherein said watermelon plant is homozygous for marker loci IIH2119, IIH5250 and IIH4836 which are genetically or physically linked to the three genetic determinants and which co-segregate with the prolific flowering trait and wherein:
 a) marker locus IIH2119 comprises a nucleotide G corresponding to position 101 of SEQ ID NO: 3;
 b) marker locus IIH5250 comprises a nucleotide A corresponding to position 101 of SEQ ID NO: 6; and
 c) marker locus IIH4836 comprises a nucleotide C corresponding to position 101 of SEQ ID NO: 9; and
wherein said three genetic determinants are as found in watermelon line SP-7, a representative seed of line SP-7 has been deposited under ATCC Accession No. PTA-123747.

2. The watermelon plant according to claim 1, wherein said plant is an inbred, a dihaploid, a hybrid, a triploid or a tetraploid plant.

3. A plant part, organ or tissue obtainable from the watermelon plant according to claim 1, including but not limited to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which comprises marker loci IIH2119, IIH5250 and IIH4836 and still exhibits the prolific flowering trait, when grown into a plant that produces fruits.

4. A seed that produces the watermelon plant according to claim 1.

5. A seed produced by the watermelon plant according to claim 1, wherein said seed comprises marker loci IIH2119, IIH5250 and IIH4836 and produces a prolific flowering watermelon plant.

6. The watermelon plant of claim 1, wherein said plant is a diploid plant.

7. A method for producing a triploid, seedless watermelon fruit, wherein the method comprises:
 (a) interplanting a diploid watermelon plant, wherein said diploid watermelon plant is the plant of claim 6, and a triploid watermelon plant; and
 (b) allowing pollination of the triploid watermelon plant by pollen of the diploid watermelon plant for production and harvesting of triploid seedless watermelon fruits.

8. A method of providing a prolific flowering watermelon plant, plant part or seed, wherein said method comprises the following steps:
 a) crossing the prolific flowering watermelon plant according to claim 1 with a watermelon plant lacking the prolific flowering trait,
 b) obtaining a plurality of progeny watermelon plants, and
 c) optionally, selecting a plant of said progeny comprising the prolific flowering trait characterized in that said selected plant comprises marker loci IIH2119, IIH5250 and IIH4836.

9. The method of claim 8, wherein the prolific flowering watermelon plant is a plant of watermelon line SP-7, representative seed of which is deposited under ATCC Accession No. PTA-123747.

10. A method for producing a prolific flowering watermelon plant wherein said method comprises the following steps:
 a) providing the seed of claim 4, wherein the seed is homozygous for marker loci IIE2119, IIH5250 and IIH4836,
 b) germinating said seed and growing a mature, fertile plant therefrom,
 c) inducing self-pollination of said fertile plant, growing fruits and harvesting fertile seeds therefrom, and
 d) growing plants from the harvested seeds and selecting a prolific flowering watermelon plant that is homozygous for marker loci IIH2119, IIH5250 and IIH4836.

11. A method of identifying the prolific flowering watermelon plant according to claim 1, wherein said method comprises the steps of:
 a) providing a watermelon population segregating for the prolific flowering trait,
 b) screening the segregating population for a member comprising marker loci IIH2119, IIH5250 and IIH4836, which co-segregate with the prolific flowering trait, and
 c) selecting a member of the segregating population which comprises marker loci IIH2119, IIH5250 and IIH4836 and the prolific flowering trait.

12. A method for increasing the number of male flowers of a watermelon plant, wherein the method comprises the steps of:
 a) selecting the prolific flowering watermelon plant according to claim 1;
 b) crossing said plant of step a), which comprises the prolific flowering trait, with a watermelon plant which does not comprise the prolific flowering trait, and
 c) selecting a progeny from said cross which comprises marker loci IIH2119, IIH5250 and IIH4836.

* * * * *